(12) United States Patent
Orome et al.

(10) Patent No.: US 9,974,516 B2
(45) Date of Patent: May 22, 2018

(54) SELECTABLE ANGLE NEEDLE GUIDE

(75) Inventors: Amir Orome, Sandy, UT (US); Eric W. Lindekugel, Salt Lake city, UT (US); Matthew W. Bown, West Bountiful, UT (US)

(73) Assignee: C. R. Bard, Inc., Murray Hill, NJ (US)

( * ) Notice: Subject to any disclaimer, the term of this patent is extended or adjusted under 35 U.S.C. 154(b) by 940 days.

(21) Appl. No.: 13/335,587

(22) Filed: Dec. 22, 2011

(65) Prior Publication Data

US 2012/0165679 A1   Jun. 28, 2012

Related U.S. Application Data

(60) Provisional application No. 61/426,297, filed on Dec. 22, 2010, provisional application No. 61/500,550, filed on Jun. 23, 2011.

(51) Int. Cl.
| | | |
|---|---|---|
| *A61B 8/00* | (2006.01) | |
| *A61B 8/08* | (2006.01) | |
| *A61B 5/15* | (2006.01) | |
| *A61B 5/153* | (2006.01) | |
| *A61B 6/12* | (2006.01) | |
| *A61B 10/02* | (2006.01) | |

(Continued)

(52) U.S. Cl.
CPC ........ *A61B 8/0841* (2013.01); *A61B 5/15003* (2013.01); *A61B 5/150175* (2013.01); *A61B 5/150748* (2013.01); *A61B 8/4444* (2013.01); *A61B 5/153* (2013.01); *A61B 6/12* (2013.01); *A61B 8/4411* (2013.01); *A61B 8/4422* (2013.01); *A61B 10/0233* (2013.01); *A61M 5/3287* (2013.01); *A61M 5/427* (2013.01)

(58) Field of Classification Search
CPC ......... A61B 5/150748; A61B 17/3403; A61M 5/427; A61M 5/46
USPC .................................................. 600/437, 461
See application file for complete search history.

(56) References Cited

U.S. PATENT DOCUMENTS

| | | | |
|---|---|---|---|
| 2,470,488 A | 5/1949 | Honerkamp et al. | |
| 4,058,114 A | 11/1977 | Soldner | |
| 4,108,165 A | 8/1978 | Kopp et al. | |

(Continued)

FOREIGN PATENT DOCUMENTS

| | | |
|---|---|---|
| CN | 3655315 | 6/2007 |
| DE | 2942405 A1 | 4/1981 |

(Continued)

OTHER PUBLICATIONS

"Linear Guides-NSK Bearings", NSK, available online Nov. 27, 2009, p. 1-3.*

(Continued)

*Primary Examiner* — Christopher Cook
(74) *Attorney, Agent, or Firm* — Rutan & Tucker, LLP

(57) ABSTRACT

A needle guide assembly for inserting a needle into the body of a patient in order to access a subcutaneous target, such as a vessel, is disclosed. In one embodiment, the needle guide assembly comprises a needle guide body that is configured to at least indirectly and removably attach to an image producing device, such as an ultrasound probe. The needle guide body defines at least first and second elongate guide channels. Each guide channel defines a unique insertion angle with respect to a longitudinal axis of the ultrasound probe. Further, each guide channel is configured to accept needles of differing gauges.

15 Claims, 10 Drawing Sheets

(51) Int. Cl.
*A61M 5/32* (2006.01)
*A61M 5/42* (2006.01)

(56) References Cited

U.S. PATENT DOCUMENTS

| | | | |
|---|---|---|---|
| 4,341,303 A * | 7/1982 | Britt | 206/343 |
| 4,346,717 A | 8/1982 | Haerten | |
| 4,363,326 A | 12/1982 | Kopel | |
| 4,402,324 A | 9/1983 | Lindgren et al. | |
| 4,408,611 A | 10/1983 | Enjoji | |
| 4,469,106 A | 9/1984 | Harui | |
| 4,497,325 A | 2/1985 | Wedel | |
| 4,548,210 A | 10/1985 | Enjoji et al. | |
| 4,576,175 A | 3/1986 | Epstein | |
| 4,582,326 A | 4/1986 | Alsip | |
| 4,608,989 A | 9/1986 | Drue | |
| 4,635,644 A | 1/1987 | Yagata | |
| 4,662,870 A | 5/1987 | Augustine et al. | |
| 4,681,103 A | 7/1987 | Boner et al. | |
| 4,723,544 A | 2/1988 | Moore et al. | |
| 4,742,829 A | 5/1988 | Law et al. | |
| 4,838,506 A | 6/1989 | Cooper | |
| 4,877,033 A | 10/1989 | Seitz, Jr. | |
| 4,883,059 A | 11/1989 | Stedman et al. | |
| 4,898,178 A | 2/1990 | Wedel | |
| 4,899,756 A | 2/1990 | Sonek | |
| 4,911,173 A | 3/1990 | Terwilliger | |
| 5,052,396 A | 10/1991 | Wedel et al. | |
| 5,076,279 A | 12/1991 | Arenson et al. | |
| 5,100,387 A | 3/1992 | Ng | |
| 5,138,748 A * | 8/1992 | Welles | 24/30.5 S |
| 5,235,987 A * | 8/1993 | Wolfe | 600/461 |
| 5,265,614 A | 11/1993 | Hayakawa et al. | |
| 5,280,427 A | 1/1994 | Magnusson et al. | |
| 5,427,108 A | 6/1995 | Bollinger | |
| D362,064 S | 9/1995 | Smick | |
| 5,494,039 A | 2/1996 | Onik et al. | |
| 5,623,931 A | 4/1997 | Wung et al. | |
| 5,758,650 A | 6/1998 | Miller et al. | |
| D399,971 S | 10/1998 | Scherer | |
| 5,911,707 A | 6/1999 | Wolvek et al. | |
| D412,032 S | 7/1999 | Mikula-Curtis et al. | |
| 5,924,992 A | 7/1999 | Park et al. | |
| 5,941,889 A | 8/1999 | Cermak | |
| 6,050,954 A | 4/2000 | Mitiermeier | |
| D424,693 S | 5/2000 | Pruter | |
| 6,083,169 A | 7/2000 | Hansen | |
| 6,095,981 A | 8/2000 | McGahan | |
| D434,850 S | 12/2000 | Balestracci | |
| 6,203,499 B1 | 3/2001 | Imling et al. | |
| 6,283,942 B1 | 9/2001 | Staehlin et al. | |
| 6,296,614 B1 | 10/2001 | Pruter | |
| 6,361,499 B1 | 3/2002 | Bates et al. | |
| 6,368,280 B1 | 4/2002 | Cermak et al. | |
| 6,379,307 B1 | 4/2002 | Filly et al. | |
| 6,425,871 B1 * | 7/2002 | Jaggi | 600/461 |
| 6,475,152 B1 | 11/2002 | Kelly, Jr. et al. | |
| 6,485,426 B2 * | 11/2002 | Sandhu | 600/461 |
| 6,612,990 B1 | 9/2003 | Pruter | |
| 6,695,786 B2 | 2/2004 | Wang et al. | |
| 6,743,177 B2 | 6/2004 | Ito et al. | |
| 6,758,817 B1 | 7/2004 | Pruter et al. | |
| 6,814,704 B2 | 11/2004 | Weilandt | |
| 6,840,954 B2 * | 1/2005 | Dietz et al. | 607/96 |
| 6,877,352 B1 | 4/2005 | Schlereth | |
| 6,884,219 B1 | 4/2005 | Pruter | |
| 6,908,433 B1 | 6/2005 | Pruter | |
| 7,022,082 B2 | 4/2006 | Sonek | |
| 7,087,024 B1 | 8/2006 | Pruter | |
| 7,322,990 B2 | 1/2008 | Mark et al. | |
| 7,351,205 B2 | 4/2008 | Szczech et al. | |
| 7,452,331 B1 | 11/2008 | Pruter | |
| 7,588,541 B2 * | 9/2009 | Floyd et al. | 600/461 |
| 7,635,336 B1 | 12/2009 | Pruter | |
| 7,670,294 B2 | 3/2010 | Kisen et al. | |
| 7,691,066 B2 | 4/2010 | Kosaku | |
| D625,802 S | 10/2010 | Choi et al. | |
| D625,805 S | 10/2010 | Hereford | |
| 7,837,627 B1 | 11/2010 | Pruter | |
| D629,898 S | 12/2010 | Bigelow | |
| D630,731 S | 1/2011 | Schmutzer et al. | |
| 7,909,815 B2 | 3/2011 | Whitmore, III et al. | |
| 7,976,469 B2 | 7/2011 | Bonde et al. | |
| D649,245 S | 11/2011 | Klebs et al. | |
| 8,073,529 B2 | 12/2011 | Cermak et al. | |
| 8,075,495 B2 | 12/2011 | Andreyko et al. | |
| 8,118,743 B2 | 2/2012 | Park et al. | |
| D655,813 S | 3/2012 | Row et al. | |
| 8,137,281 B2 | 3/2012 | Huang et al. | |
| D659,825 S | 5/2012 | Dillard, III | |
| D672,460 S | 12/2012 | Baid | |
| 8,430,889 B2 | 4/2013 | Zeng et al. | |
| D683,019 S | 5/2013 | Shahidi Bonjar | |
| 8,496,593 B2 | 7/2013 | Park et al. | |
| 8,523,824 B2 | 9/2013 | Teirstein et al. | |
| 8,641,620 B2 | 2/2014 | Lasser et al. | |
| 8,647,280 B2 | 2/2014 | Ooiishi et al. | |
| 8,696,583 B2 | 4/2014 | Ohgishi et al. | |
| 8,696,585 B2 | 4/2014 | Addison et al. | |
| 8,708,916 B2 | 4/2014 | Okuno | |
| 8,740,800 B2 | 6/2014 | Wakabayashi et al. | |
| 8,747,324 B1 | 6/2014 | Pruter et al. | |
| D710,995 S | 8/2014 | Shirley et al. | |
| 8,795,183 B2 | 8/2014 | Siebrecht et al. | |
| 8,808,186 B2 | 8/2014 | Fruland et al. | |
| D727,495 S | 4/2015 | Bown et al. | |
| 9,788,812 B2 | 10/2017 | Orome et al. | |
| 2002/0123689 A1 | 9/2002 | Furia | |
| 2002/0133079 A1 | 9/2002 | Sandhu | |
| 2003/0144627 A1 | 7/2003 | Woehr et al. | |
| 2003/0195425 A1 | 10/2003 | Ito | |
| 2004/0133111 A1 | 7/2004 | Szczech et al. | |
| 2005/0059891 A1 | 3/2005 | Kosaku | |
| 2005/0113816 A1 | 5/2005 | Whitmore et al. | |
| 2005/0143753 A1 | 6/2005 | Whitmore et al. | |
| 2005/0267373 A1 | 12/2005 | Lee | |
| 2006/0129046 A1 | 6/2006 | Stevens et al. | |
| 2006/0150876 A1 | 7/2006 | Green et al. | |
| 2006/0241477 A1 | 10/2006 | Sasady et al. | |
| 2007/0016781 A1 | 1/2007 | Asokan et al. | |
| 2007/0038113 A1 | 2/2007 | Oonuki et al. | |
| 2007/0073155 A1 | 3/2007 | Park et al. | |
| 2007/0078346 A1 | 4/2007 | Park et al. | |
| 2007/0112272 A1 | 5/2007 | Park et al. | |
| 2007/0167817 A1 | 7/2007 | Huang et al. | |
| 2007/0276241 A1 | 11/2007 | Park et al. | |
| 2007/0276253 A1 | 11/2007 | Park et al. | |
| 2007/0282205 A1 | 12/2007 | Furia | |
| 2008/0033454 A1 | 2/2008 | Lukoschek et al. | |
| 2008/0300491 A1 | 12/2008 | Bonde et al. | |
| 2009/0143684 A1 | 6/2009 | Cermak et al. | |
| 2009/0171219 A1 | 7/2009 | Uchibori | |
| 2009/0247876 A1 | 10/2009 | Cannon, Jr. et al. | |
| 2009/0266957 A1 | 10/2009 | Cermak | |
| 2009/0270722 A1 | 10/2009 | Floyd et al. | |
| 2009/0275833 A1 | 11/2009 | Ikeda et al. | |
| 2010/0010475 A1 | 1/2010 | Teirstein et al. | |
| 2010/0041990 A1 * | 2/2010 | Schlitt et al. | 600/439 |
| 2010/0081920 A1 | 4/2010 | Whitmore, III et al. | |
| 2010/0106056 A1 | 4/2010 | Norris | |
| 2010/0160787 A1 | 6/2010 | Gorzitze | |
| 2010/0228131 A1 | 9/2010 | Oonuki et al. | |
| 2010/0247513 A1 | 9/2010 | Agee et al. | |
| 2010/0312121 A1 | 12/2010 | Guan | |
| 2011/0028847 A1 | 2/2011 | Whitmore, III et al. | |
| 2012/0330159 A1 | 12/2012 | Orome et al. | |
| 2013/0150714 A1 | 6/2013 | Howlett et al. | |
| 2013/0245452 A1 | 9/2013 | Gorzitze | |
| 2015/0025315 A1 | 1/2015 | Nishina et al. | |
| 2015/0112200 A1 | 4/2015 | Oberg et al. | |

(56) References Cited

U.S. PATENT DOCUMENTS

FOREIGN PATENT DOCUMENTS

| | | | |
|---|---|---|---|
| EP | 1709919 A1 | 10/2006 |
| JP | 01097440 A | 4/1989 |
| JP | 03173542 A | 7/1991 |
| JP | 11128237 A | 5/1999 |
| JP | 21161683 | 6/2001 |
| JP | 21340334 | 12/2001 |
| JP | 23299654 | 10/2003 |
| JP | 23334191 | 11/2003 |
| JP | 2005-034273 A | 2/2005 |
| JP | D1268564 | 4/2006 |
| JP | 2009-153831 A | 7/2009 |
| JP | 2010-115246 A | 5/2010 |
| WO | 1996010958 A2 | 4/1996 |
| WO | 2000019906 | 4/2000 |
| WO | 2000040155 A1 | 7/2000 |
| WO | 2003094701 A2 | 11/2003 |
| WO | 2004021898 A1 | 3/2004 |
| WO | 2006060657 A2 | 6/2006 |
| WO | 2007027511 A2 | 3/2007 |
| WO | 2007040172 A1 | 4/2007 |
| WO | 2007110076 A1 | 10/2007 |
| WO | 2008024515 A2 | 2/2008 |
| WO | 2009073653 A1 | 6/2009 |
| WO | 2009090230 A1 | 7/2009 |
| WO | 2010080637 A1 | 7/2010 |
| WO | 2010084322 A1 | 7/2010 |
| WO | 2012088458 | 6/2012 |
| WO | 2012178109 | 12/2012 |
| WO | 2013054168 A2 | 4/2013 |
| WO | 2015100332 A1 | 7/2015 |

OTHER PUBLICATIONS

"Slide-N-Lock Tie-Down Systems", Hoover Fence Co., available online Dec. 2, 2008, pp. 1-2.*
PCT/US2011/066940 filed Dec. 22, 2011 International Search Report and Written Opinion dated Apr. 20, 2012.
PCT/US2009/068828 filed Dec. 18, 2009 International Preliminary Report on Patentability dated Jun. 21, 2011.
PCT/US2009/068828 filed Dec. 18, 2009 Search Report dated Mar. 3, 2010.
PCT/US2009/068828 filed Dec. 18, 2009 Written Opinion dated Mar. 3, 2010.
PCT/US2011/066940 filed Dec. 22, 2011 International Preliminary Report on Patentability dated Jul. 4, 2013.
PCT/US2012/043877 filed Jun. 22, 2012 International Search Report and Written Opinion dated Sep. 24, 2012.
U.S. Appl. No. 12/642,456, filed Dec. 18, 2009 Final Office Action dated Nov. 23, 2012.
U.S. Appl. No. 12/642,456, filed Dec. 18, 2009 Non-Final Office Action dated Jul. 2, 2012.
U.S. Appl. No. 12/642,456, filed Dec. 18, 2009 Notice of Allowance dated Jul. 12, 2013.
U.S. Appl. No. 13/886,196, filed May 2, 2013 Final Office Action dated Apr. 10, 2014.
U.S. Appl. No. 13/886,196, filed May 2, 2013 Non-Final Office Action dated Dec. 19, 2013.
U.S. Appl. No. 13/886,196, filed May 2, 2013 Advisory Action dated Jun. 13, 2014.
U.S. Appl. No. 13/886,196, filed May 2, 2013 Non-Final Office Action dated Jul. 25, 2014.
CN 201180067467.2 filed Aug. 13, 2013 First Office Action dated Sep. 4, 2014.
EP 11 850 516.3 filed Jul. 19, 2013 Extended European Search Report dated Mar. 4, 2015.
EP 12 803 493.1 filed Jan. 15, 2014 Extended European Search Report dated Mar. 5, 2015.
U.S. Appl. No. 13/531,406, filed Jun. 22, 2012 Non-Final Office Action dated Jan. 9, 2015.
U.S. Appl. No. 13/886,196, filed May 2, 2013 Final Office Action dated Dec. 22, 2014.
U.S. Appl. No. 13/886,196, filed May 2, 2013 Examiner's Answer dated Nov. 3, 2015.
U.S. Appl. No. 29/493,150, filed Jun. 5, 2014 Notice of Allowance dated Oct. 29, 2015.
JP 2013-546435 filed Jun. 6, 2013 Office Action dated Aug. 29, 2016.
JP 2014-517229 filed Dec. 20, 2013 Notice of Allowance dated Oct. 3, 2016.
U.S. Appl. No. 13/531,406, filed Jun. 22, 2012 Non-Final Office Action dated Aug. 10, 2016.
CN 201280030885.9 filed Dec. 23, 2013 Second Office Action dated Nov. 4, 2015.
CN 201280030885.9 filed Dec. 23, 2013 Third Office Action dated May 5, 2016.
JP 2014-517229 filed Dec. 20, 2013 First Office Action dated May 24, 2016.
U.S. Appl. No. 13/531,406, filed Jun. 22, 2012 Advisory Action dated May 3, 2017.
U.S. Appl. No. 13/531,406, filed Jun. 22, 2012 Notice of Allowance dated Jun. 20, 2017.
U.S. Appl. No. 14/581,019, filed Dec. 23, 2014 Non-Final Office Action dated Apr. 12, 2017.
CN 201180067461.2 filed Aug. 13, 2013 second Office Action dated Apr. 30, 2015.
CN 201180067467.2 filed Aug. 13, 2013 Third Office Action dated Oct. 28, 2015.
CN 201280030885.9 filed Dec. 23, 2013 First Office Action dated Mar. 3, 2015.
PCT/US2014/072168 filed Dec. 23, 2014 International Search Report and Written Opinion dated Apr. 16, 2015.
U.S. Appl. No. 13/531,406, filed Jun. 22, 2012 Final Office Action dated Feb. 25, 2016.
U.S. Appl. No. 13/531,406, filed Jun. 22, 2012 Non-Final Office Action dated Aug. 18, 2015.
EP 14875859.2 filed Jun. 9, 2016 Extended European Search Report dated Jul. 31, 2017.

* cited by examiner

SELECTABLE ANGLE NEEDLE GUIDE

CROSS-REFERENCE TO RELATED APPLICATIONS

This application claims the benefit of U.S. Provisional Patent Application No. 61/426,297, filed Dec. 22, 2010, titled "Selectable Angle needle Guide," and U.S. Provisional Patent Application No. 61/500,550, filed Jun. 23, 2011, titled "Needle Guide with Selectable Aspects," each of which is incorporated herein by reference in its entirety.

BRIEF SUMMARY

Briefly summarized, embodiments of the present invention are directed to a needle guide assembly for inserting a needle into the body of a patient in order to access a subcutaneous target, such as a vessel. In one embodiment, the needle guide assembly comprises a needle guide body that is configured to at least indirectly and removably attach to an image producing device, such as an ultrasound probe. The needle guide body defines at least first and second elongate guide channels. Each guide channel defines a unique insertion angle with respect to a longitudinal axis of the ultrasound probe. Further, each guide channel is configured to accept needles of differing gauges.

In addition, other needle guide assemblies are disclosed that include multiple guide channels for inserting a needle at a variety of insertion angles into the patient's body. Related methods are also disclosed.

These and other features of embodiments of the present invention will become more fully apparent from the following description and appended claims, or may be learned by the practice of embodiments of the invention as set forth hereinafter.

BRIEF DESCRIPTION OF THE DRAWINGS

A more particular description of the present disclosure will be rendered by reference to specific embodiments thereof that are illustrated in the appended drawings. It is appreciated that these drawings depict only typical embodiments of the invention and are therefore not to be considered limiting of its scope. Example embodiments of the invention will be described and explained with additional specificity and detail through the use of the accompanying drawings in which.

DETAILED DESCRIPTION OF SELECTED EMBODIMENTS

Reference will now be made to figures wherein like structures will be provided with like reference designations. It is understood that the drawings are diagrammatic and schematic representations of exemplary embodiments of the present invention, and are neither limiting nor necessarily drawn to scale. It is to be understood that the words "including," "has," and "having," as used herein, including the claims, shall have the same meaning as the word "comprising."

Embodiments of the present invention are generally directed to a needle guide assembly for guiding a needle or other elongate implement into a body of a patient. In one embodiment, the needle guide is removably attached in a direct or indirect manner to an ultrasound probe so as to enable insertion of the needle via the needle guide assembly while an intended subcutaneous target of the needle is being imaged by the ultrasound probe. Further, in one embodiment, the needle guide assembly includes multiple differently angled needle guide channels that are selectable by a user to enable the needle to be directed at a desired angle into the patient's body toward the subcutaneous target. Thus, the ability to direct a needle at a variety of angles with a single guide assembly is achieved.

FIGS. 1A-1D depict one example of a needle guide assembly, generally designated at 10, according to one embodiment. As shown, the needle guide assembly 10 includes a body 12 for attaching the assembly to an image producing device, as will be described further below. In one embodiment, the image producing device includes a hand-held probe of an ultrasound imaging device, though other imaging devices can also be utilized, such x-ray and MRI-based systems, for example. Optionally, the needle guide assembly can be attached to other components in addition to image producing devices. The needle guide body 12 in the present embodiment includes thermoplastic, but in other embodiments other materials can be employed, including other types of plastic, metals, metal alloys, ceramics, etc.

Figure 1A:
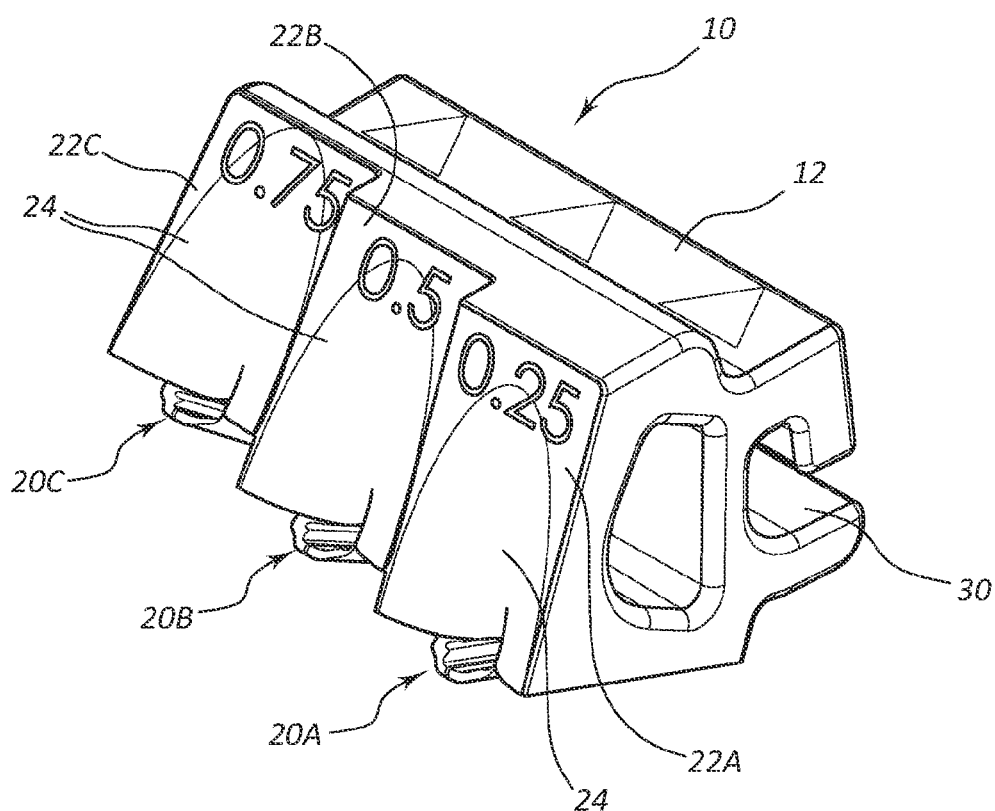
FIGS. 1A-1D are various views of a needle guide assembly according to one embodiment.
Figure 1B:
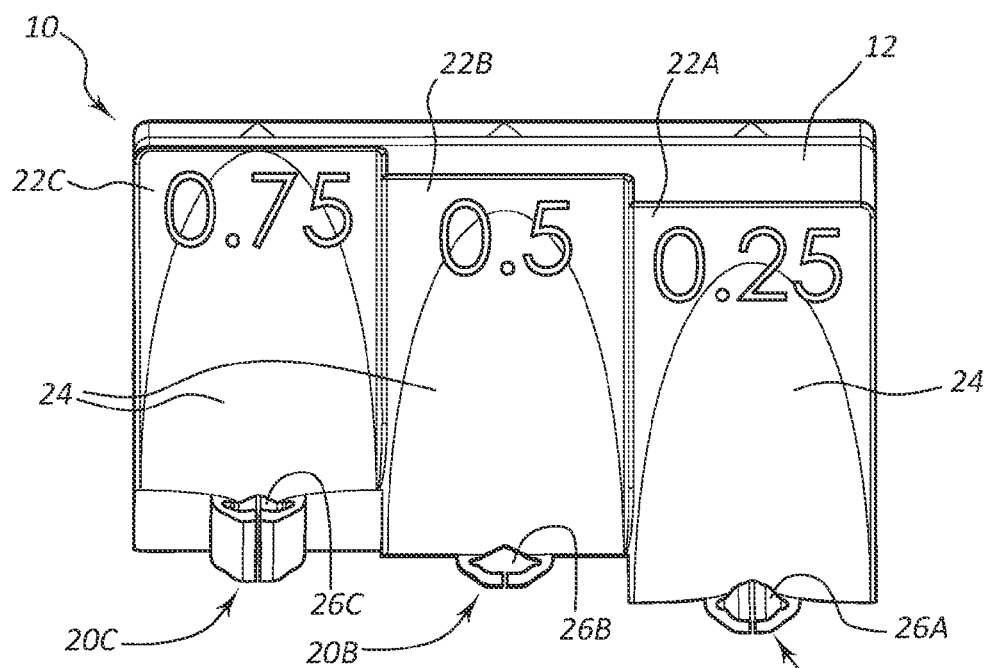
Figure 1C:
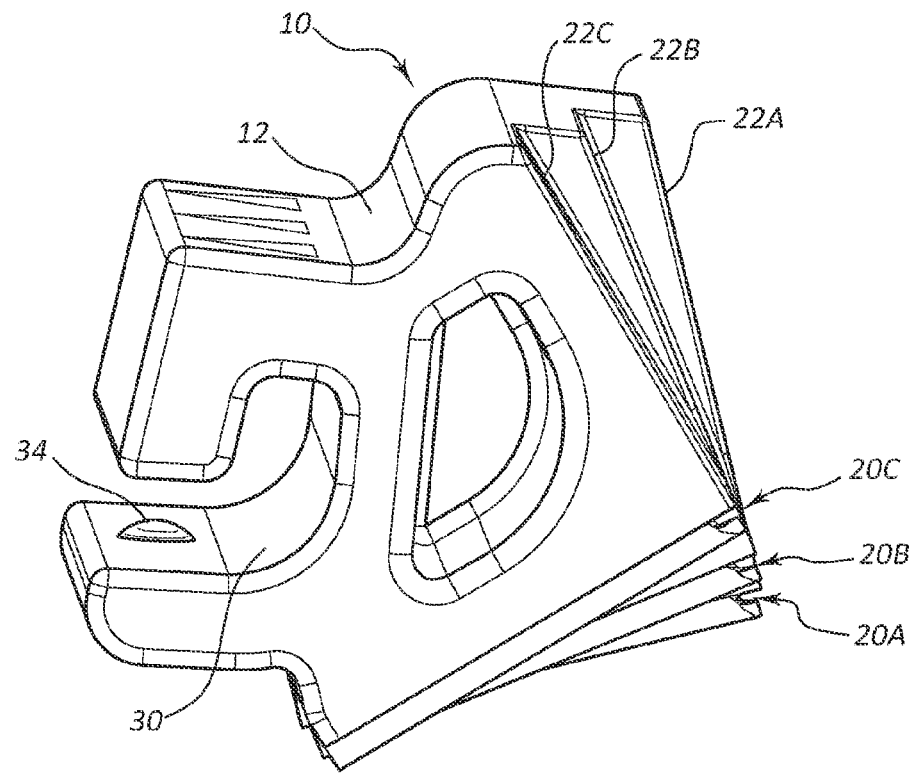

As shown in the perspective shown in FIGS. 1A and 1B, the needle guide body 12 in the present embodiment defines three front faces 22A, 22B, and 22C. At the bottom of each of the front faces 22A-22C, a corresponding guide channel 20A, 20B, and 20C is defined. Each guide channel 20A-20C defines a unique angle of attack, or needle insertion angle, for a needle disposed therein. Correspondingly, each front face 22A-22C is oriented so as to be disposed at substantially a right angle with the longitudinal length of the respective guide channel 20A-20C, as best seen in FIG. 1C. As will be seen further below, the unique angling of each guide channel facilitates proper placement of a needle into a patient so as to access a desired target at a particular subcutaneous depth, such as a vessel, for instance.

Each of the front faces 22A-22C includes a concavely shaped contoured surface 24 that slopes toward an open proximal end 26A, 26B, 26C of the respective guide channel 20A-20C. The contoured surfaces 24 assist in guiding a needle tip placed thereon toward the respective guide channel proximal end opening, thus easing needle insertion into the guide channel. It is appreciated that the front faces can be contoured in other ways as well.

Figure 1D:
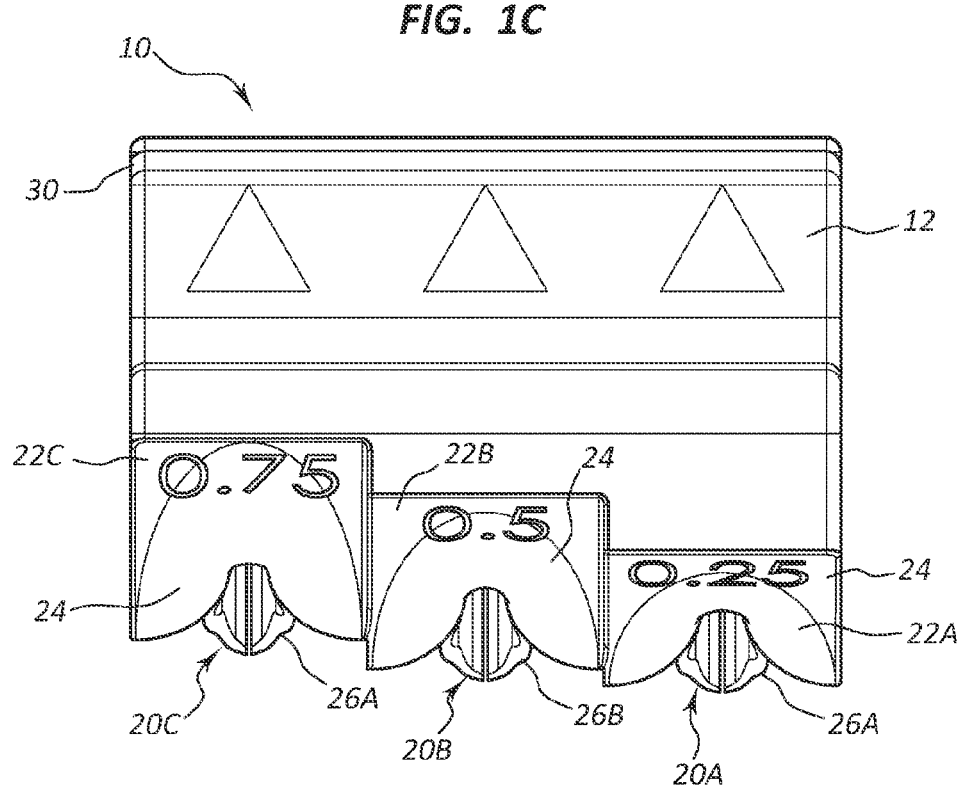

Also, as best seen in FIG. 1D, the proximal ends 26A-26C of the guide channels 20A-20C extend slightly proximal to the respective front faces 22A-22C so as to further ease insertion of the needle tip into the particular guide channel.

The needle guide assembly 10 in the present embodiment is configured so as to be movable with respect to the ultrasound probe or other device with which it is connected. FIGS. 1A and 1C show one implementation of this, wherein the needle guide body 12 includes a track 30 configured to slidably engage a rail 60 (FIGS. 4 and 5) associated with the probe, thus enabling the needle guide body to slide with respect to the probe, as will be further discussed below. As shown, the track 30 includes an L-shaped configuration to assist the needle guide in remaining physically engaged with the rail 60. Note that this is but one example of fixtures to provide connection between the probe and the needle guide; indeed, various other connection schemes can be employed. In addition, it is appreciated that the needle guide can be indirectly or indirectly and temporarily or permanently attached to other surfaces of the ultrasound probe, including side surfaces, end surfaces, etc.

Figure 2:
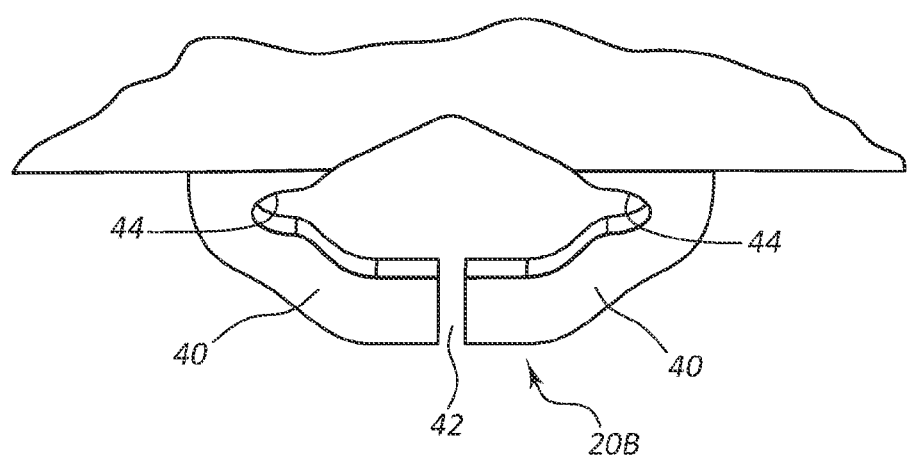
FIG. 2 is an end view of a guide channel of the needle guide assembly of FIGS. 1A-1D.

FIG. 2 shows a proximal end view of the guide channel 20B, which is representative of the other guide channels 20A and 20C, and thus the description here equally applies to each guide channel. As shown, the guide channel 20B includes two arms 40 that each extend distally from the proximal end 26B along the length of the needle guide body 12 to enclose an elongate volume into which a portion of the needle is disposed when the needle is inserted into the guide channel 20B. Cross sectionally, the arms 40 are shaped to extend from the needle guide body 12 and terminate toward each other such that an opening 42 is defined between the terminal arm ends. The opening 42 runs the entire length between the arms 40 so as to define a slot through which a needle or other suitable elongate device can be removed from the guide channel 20A-20C when desired. Notches 44 are also included in each arm 40 proximate attachment of the arm with the main portion of the needle guide body 12. The shape of the arms 40, together with the notches 44, enables the guide channel 20B to expand when needed to receive therewithin needles of a variety of gauges. This in turn offers flexibility for the needle guide 10 and enables it to be used to guide a variety of needles into the patient while still maintaining a suitable amount of directional constraint for the needle such that it enters the patient's body at the intended needle insertion angle. The notches 44 are particularly suited to facilitating expansion of the channel size while maintaining suitable amounts of force imposed on the needle by the arms 40, resulting in the above-mentioned constraint. Note that in one embodiment at least the arms 40 include a thermoplastic or other suitably compliant material to enable bending thereof, as just described.

It is appreciated that the number, size, shape, placement, etc. of the guide channels on the needle guide can vary from what is shown and described herein. Further, though all are similarly configured in the embodiment of FIGS. 1A-1D, it is appreciated that the particular configuration of the guide channels can vary one from another on the same needle guide. Thus, these and other expansions of the principles discussed herein are contemplated.

Figure 3:
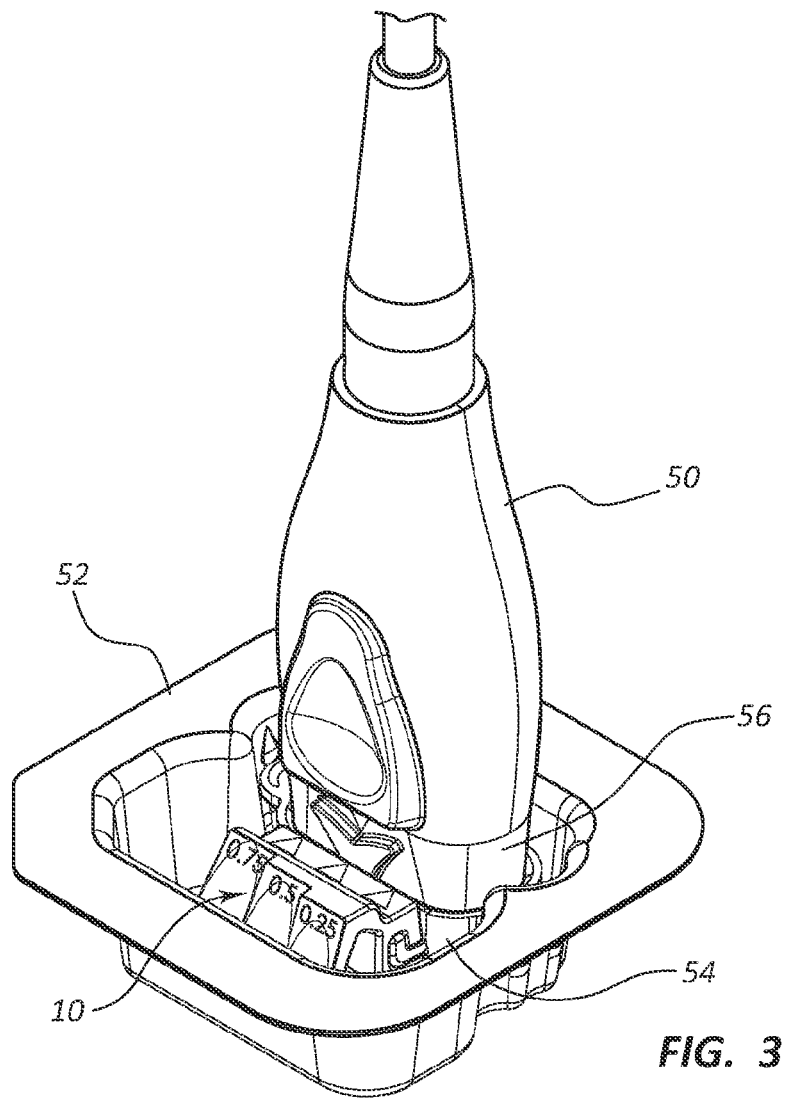
FIG. 3 is a perspective view of a needle guide assembly attached to an ultrasound probe according to one embodiment.

FIG. 3 shows the needle guide assembly 10 disposed in a storage tray 52 together with a probe cap 54. An ultrasound probe 50 is shown with a head thereof removably inserted into the probe cap 54, in preparation for removing the probe cap and the needle guide assembly 10 from the tray 52. As such, it is appreciated that in the present embodiment the tray 52 is an example of a manner in which the needle guide assembly can be packaged, sterilized, and stored prior to use by a clinician, though other packaging configurations are also contemplated.

Figure 4:
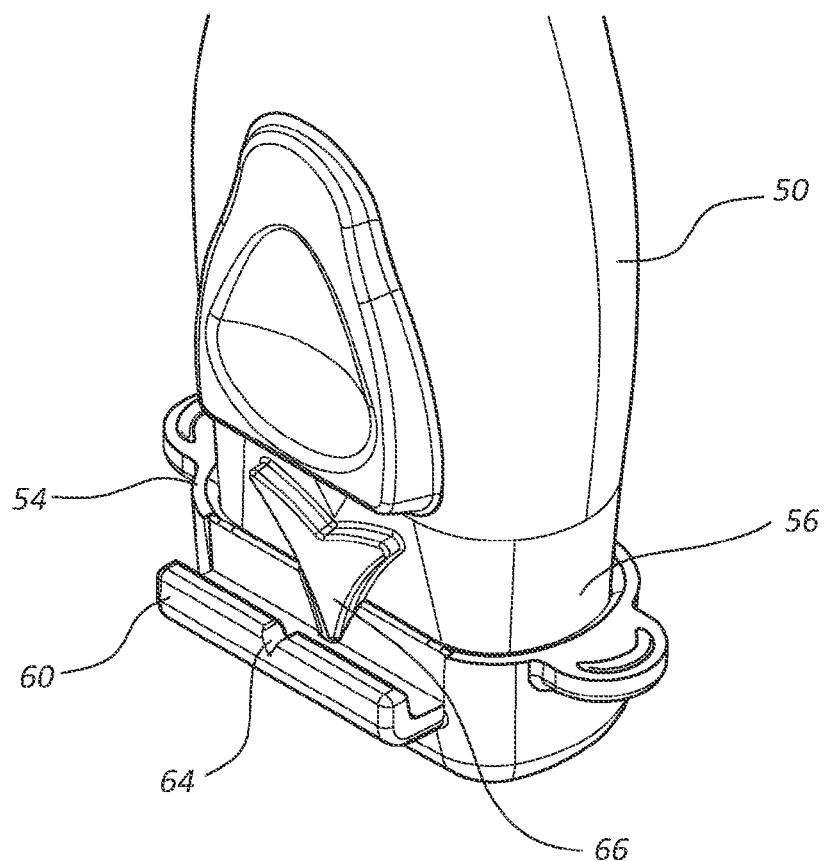
FIG. 4 is a perspective view of a cap attached to an ultrasound probe according to one embodiment.
Figure 5:
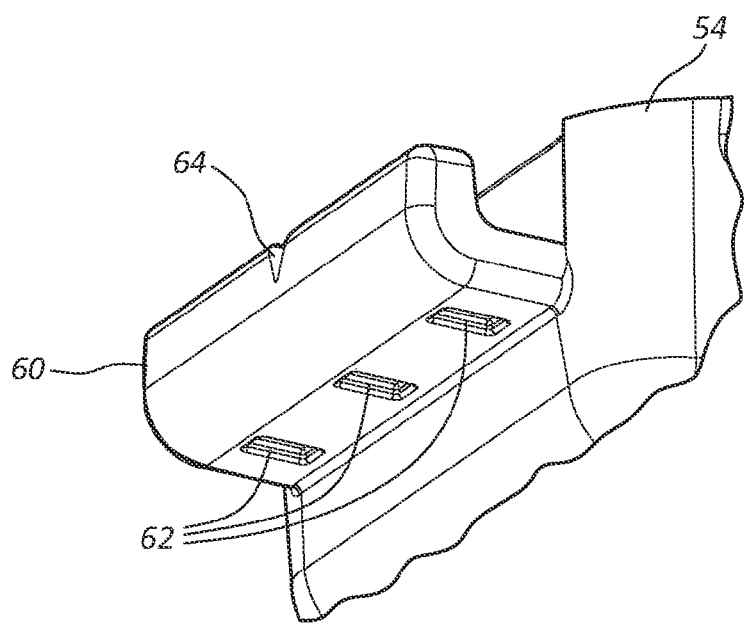
FIG. 5 is a perspective view of a portion of the probe cap of FIG. 4.

FIG. 4 shows the manner of attachment of a head portion 56 of the ultrasound probe 50 with the probe cap 54. FIGS. 4 and 5 show details of the rail 60 that extends from the probe cap 54 and serves as a fixture for attachment of the needle guide assembly 10 thereto. Note that, though a probe cap is used here for attachment, in other embodiments the needle guide assembly can be attached directly to the probe itself, or directly/indirectly to another device. Further details regarding probe caps with which the needle guide assembly described herein can be used can be found in U.S. Patent Publication No. 2011/0313293, filed Aug. 9, 2011, and entitled "Support and Cover Structures for an Ultrasound Probe Head," which is incorporated herein by reference in its entirety.

Figure 6:
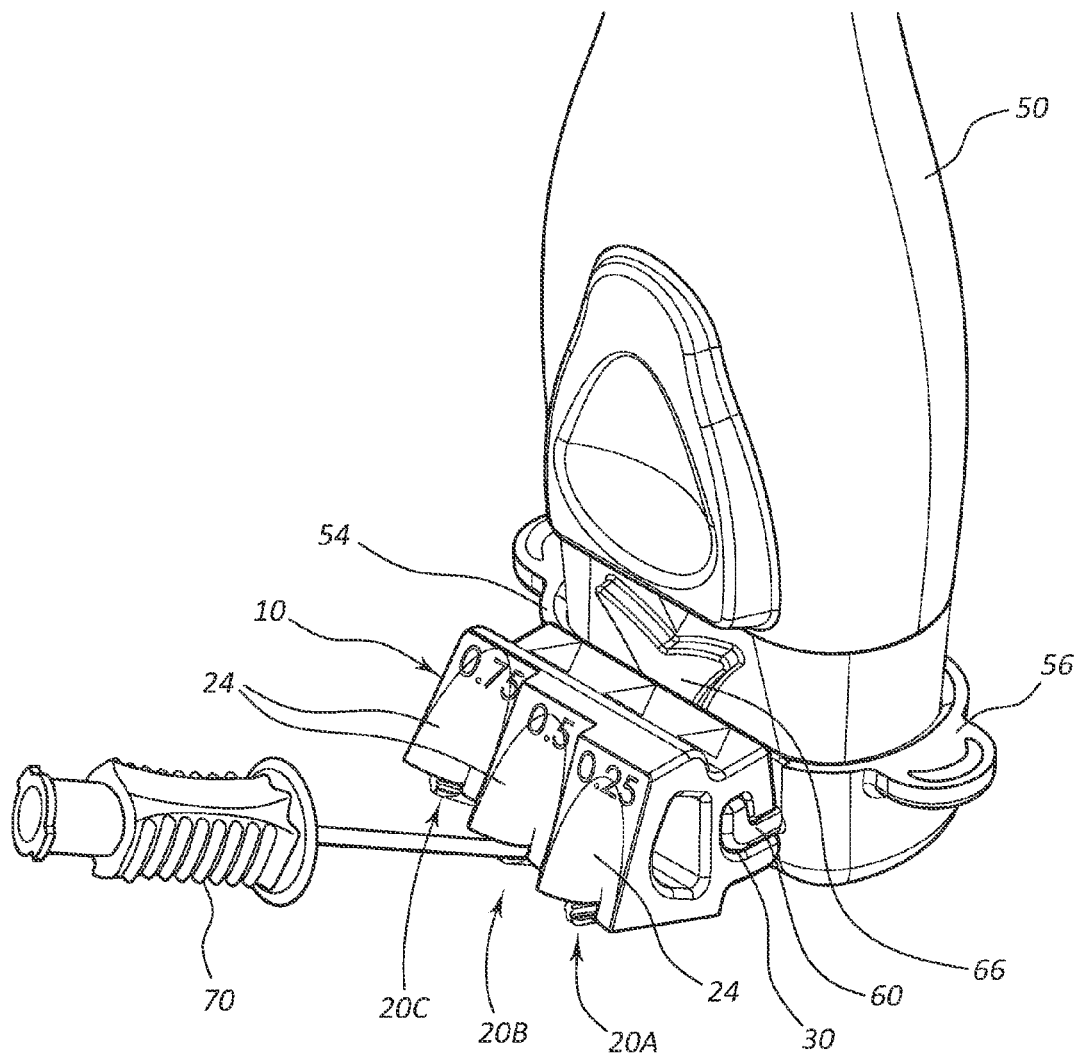
FIG. 6 is a perspective view of the needle guide assembly of FIGS. 1A-1D attached to the probe cap of FIGS. 3 and 4 in a first position.

As shown, the rail 60 includes an L-shaped cross sectional shape to match the shape of the track 30 and to assist in maintaining engagement with the needle guide assembly 10, though it is appreciated that other rail shapes can also be employed. FIG. 6 shows the rail 60 of the probe cap 54 slidably inserted into the track 30 defined by the needle guide assembly 10 such that needle guide assembly is in position for use in guiding a needle into the body of a patient. Note that the probe 50 includes an arrow 66 that indicates the lateral center of the device, for alignment purposes during use. As best seen in FIG. 4, a notch 64 is included on the rail 60 that is aligned with the probe arrow 66 when the probe cap 54 is properly attached the probe 50, and can be used to assist the clinician in aligning a needle with the center of the probe head 56 when no needle guide is used.

FIG. 5 shows that a plurality of detents 62 are included on the rail 60. The detents 62 are spaced so as to individually engage with a nub 34, disposed in the track 30 (FIG. 1C) when a respective one of the guide channels 20A-20C are aligned with the arrow 66 of the probe 50, i.e., in position to guide a needle into the body of the patient.

With the needle guide assembly 10 attached to the probe cap 54 of the probe 50 via the track 30 and rail 60 engagement described above and as shown in FIG. 6, the needle guide assembly can be employed to guide a needle into the body of a patient. As mentioned and as seen in FIG. 6, each guide channel 20A-20C defines a unique needle insertion angle with respect to a longitudinal axis of the probe 50 (or, optionally, the skin surface of the patient when the cap-covered probe head 56 is positioned against the skin in the orientation shown in FIG. 6). The front faces 22A-22C of the needle guide body 12 in FIG. 6 are marked with a depth number indicating the depth at which a needle inserted through the corresponding guide channel 20A-20C would intercept the plane of the image produced by the ultrasound probe.

Thus, in the configuration shown in FIG. 6, the guide channel 20B is aligned with the probe arrow 66 such that a needle 70 that is passed therethrough enters the center of the image produced by the probe 50. As indicated on its front face 22B, the needle insertion angle of the guide channel 20B is such that the needle 70 will intercept the image plane of the probe 50 approximately 0.5 cm below the surface of the skin.

Thus, during an ultrasound imaging procedure, a clinician can observe an image produced by the ultrasound probe of an intended subcutaneous target, such as a vein, when the probe is placed against the skin of the patient. Once the target is imaged by the probe, the clinician can inspect the image and determine or observe the depth of the target under the skin. The clinician can then laterally slide the needle guide body along the probe rail 60 until the guide channel 20A-20C that is marked with a depth corresponding to the depth of the target is aligned with the center of the probe, indicated by the arrow 66 on the probe head 56. Note that the needle guide body 12 is maintained in the selected position via engagement of the nub 34 in the track 30 (FIG. 1C) with the corresponding detent 62 on the rail 60 (FIG. 5). In the configuration shown in FIG. 6, for example, the nub 34 is engaged with the middle detent 62 so as to maintain the guide channel 20B aligned with the center of the probe 50 indicated by the arrow 66. The needle 70 can then be inserted into the selected guide channel 20A-20C (e.g., guide channel 20B in the example shown in FIG. 6) and with continued use of the ultrasound image, the needle can be guided to the intended subcutaneous target.

Figure 7:
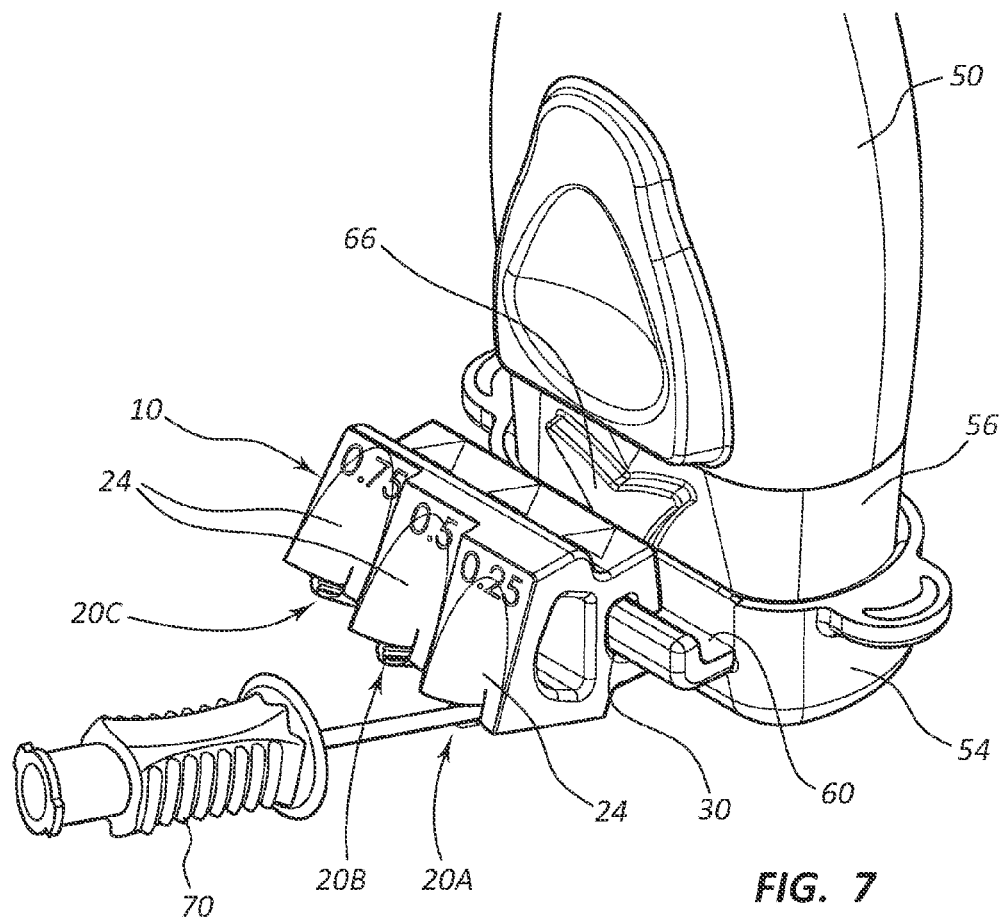
FIG. 7 is a perspective view of the needle guide assembly of FIGS. 1A-1D attached to the probe cap of FIGS. 3 and 4 in a second position.

If a deeper or shallower insertion angle is desired in order to access a deeper or shallower target, respectively, the needle guide assembly 10 can be laterally slid so that the guide channel having the desired target interception depth as marked on the front face 22A-22C is centered with the probe arrow 66. A needle or other suitable elongate instrument can then be inserted through the guide channel and into the patient's skin while the probe 50 is held in place against the skin to continue imaging the target. This is illustrated in FIG. 7, wherein the needle guide assembly 10 is positioned as described and the needle 70 is inserted through the guide channel 20A so as to intercept the ultrasound imager plane at a depth under the skin of approximately 0.25 cm. Note the relatively more shallow needle insertion angle of the guide channel 20A (as evidenced by the less steeply angled needle 70) in FIG. 7 in comparison with the needle insertion angle of the guide channel 20B in FIG. 6.

As described above, each guide channel 20A-20C includes a slot defined by the longitudinal opening 42 between the guide channel arms 40 (FIGS. 1B, 2). Once the target has been accessed, the needle 70 can be removed from engagement with the needle guide assembly 10 by gently pulling the assembly away from the needle such that the needle pulls through the slot of the guide channel 20A-20C and separates from the needle guide assembly.

Figure 8:
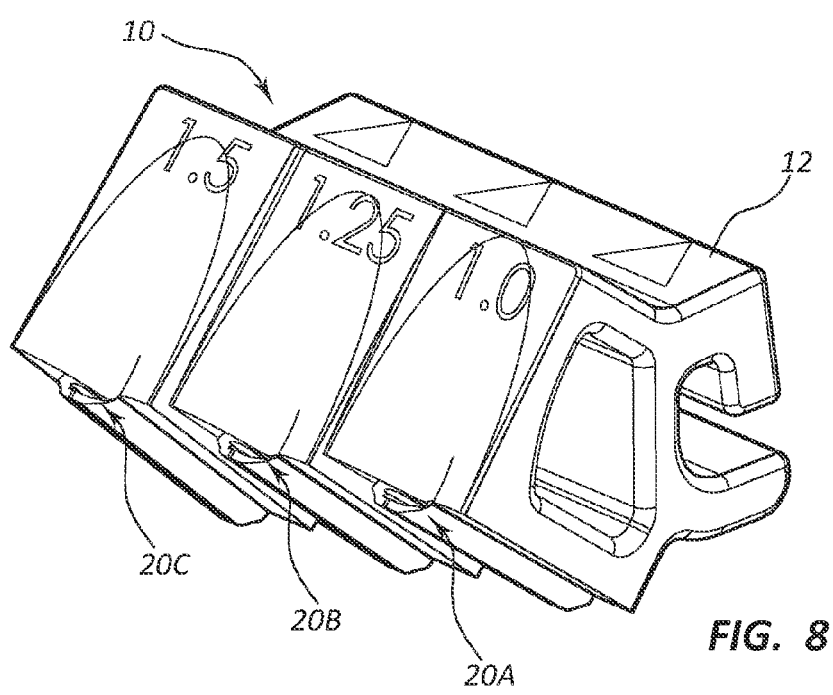
FIG. 8 is a perspective view of a needle guide assembly according to one embodiment.

As was mentioned, the needle guide assembly 10 can include guide channels defining other needle insertion angles and corresponding image plane interception depths. One example of this is shown in FIG. 8, wherein the needle guide assembly body 12 defines needle guide channels 20A, 20B, and 20C that include relatively steeper needle insertion angles than those of the assembly shown in FIGS. 1A-1D, which are useful for accessing relatively deeper subcutaneous targets within the body of the patient. Thus, it is appreciated that guide channels of a variety of needle insertion angles can be included on the needle guide. In addition, the needle guide assembly can define different numbers and positions of guide channels other than what is explicitly shown and described herein. Moreover, the various guide channels and/or front faces corresponding thereto can be color-coded to assist the user in selecting a desired insertion angle. It is also appreciated that, though disclosed herein as being able to accommodate needles of multiple gauges, the guide channels of the needle guide assemblies of other embodiments can be configured for accommodating needles of only a single gauge, if desired. These and other variations to the needle guide assembly are therefore contemplated.

Figure 9A:
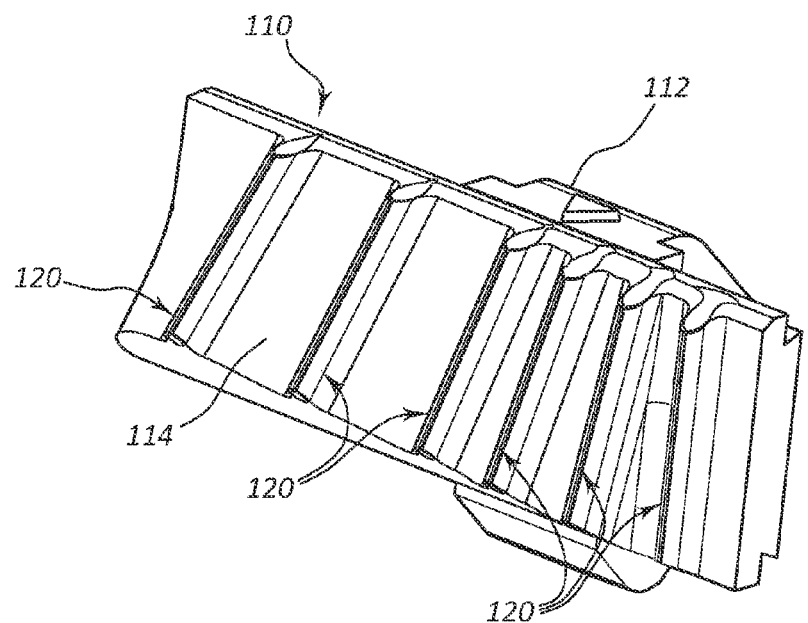
FIGS. 9A-9C are various views of a needle guide assembly according to one embodiment.
Figure 9B:
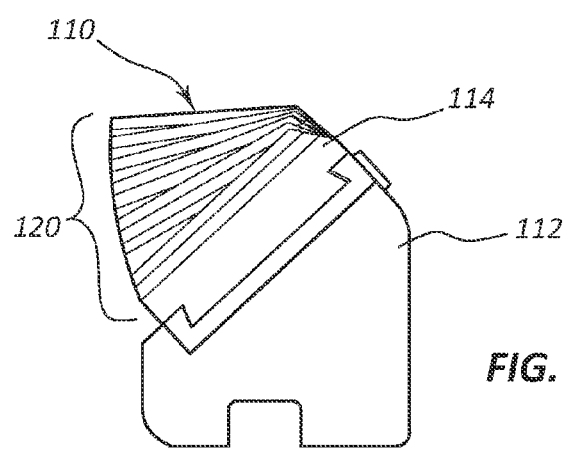
Figure 9C:
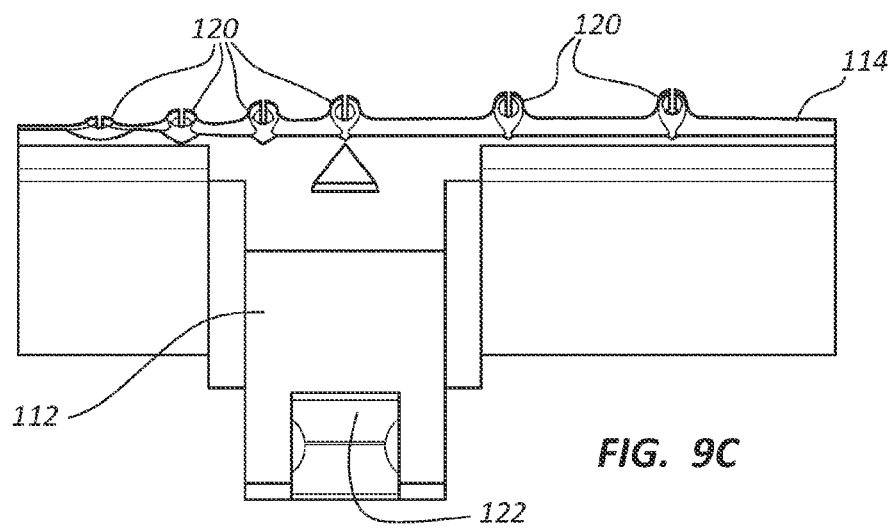

FIGS. 9A-9C depict details of a needle guide assembly 110, according to another embodiment, including a base 112 defining a cavity 122 for attaching the assembly to a corresponding fixture on an ultrasound probe or other suitable device, and a platform 114. The platform 114 includes a plurality of differently angled guide channels 120 and is slidably attached to the base 112 so as to enable the platform to slide laterally with respect to the base.

In greater detail, the platform 114 is shaped such that each guide channel 120 defines a unique needle insertion angle for a needle disposed therein. As with the needle guide assembly of FIGS. 1A-1D, the needle guide assembly 110 is slidably adjustable with respect to the ultrasound probe to enable the clinician to laterally slide the platform 114 of the assembly until the guide channel 120 that matches the required depth to the intended subcutaneous target as imaged by the probe is aligned with the center of the probe. The needle can then be inserted into the selected guide channel 120 and with continued use of the ultrasound imaging, the needle can be guided to the intended target. Note again that, as with the other embodiments herein, the number, shape, angle, and configuration of the needle guide channels can vary from what is shown and described. Note also that the needle guide assemblies herein can be configured to guide other elongate implements in addition to needles. Further, note that the needle guide assembly can be configured such that the guide channel to be used is positioned at some point other than at the lateral center of the ultrasound probe or other device to which the assembly is operably attached.

FIG. 9B shows the dovetail-type engagement of the platform 114 with the base 112 to enable relative sliding therebetween. Nubs or other interference features can be included on the base 112, the platform 114, or both to enable each guide channel 120 to lock into place when positioned for use. The base 112 can be removable from the ultrasound probe/cap via a snap-fit engagement of the cavity 112 thereof with a suitable fixture on the probe, or permanently affixed thereto. Note that the design of the cavity and fixture can vary from what is shown and described herein, as may be appreciated. In other embodiments the platform can include a semi-circular, parabolic, elliptical, or other non-linear shape to enable the platform to arcuately or otherwise slide about the base. Note that the dovetail-type engagement between the platform and the base can be replaced by other engagement schemes that enable relative movement therebetween.

Figure 10A:
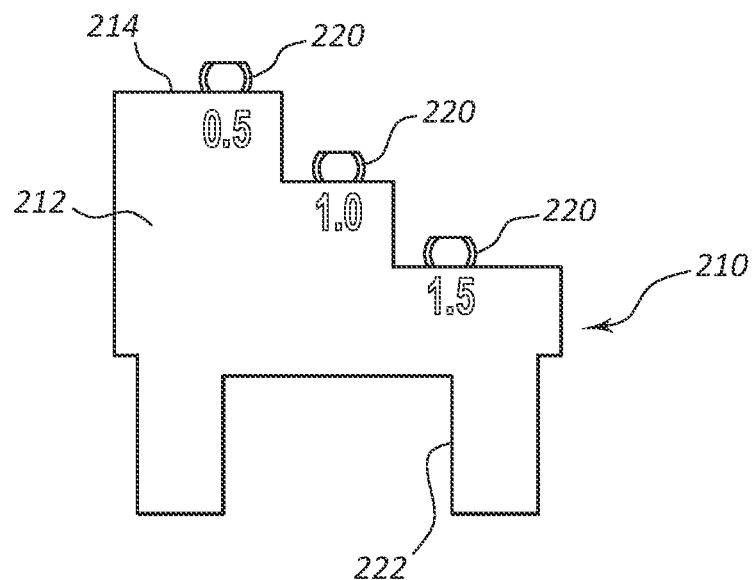
FIGS. 10A and 10B are various views of a needle guide assembly according to one embodiment.
Figure 10B:
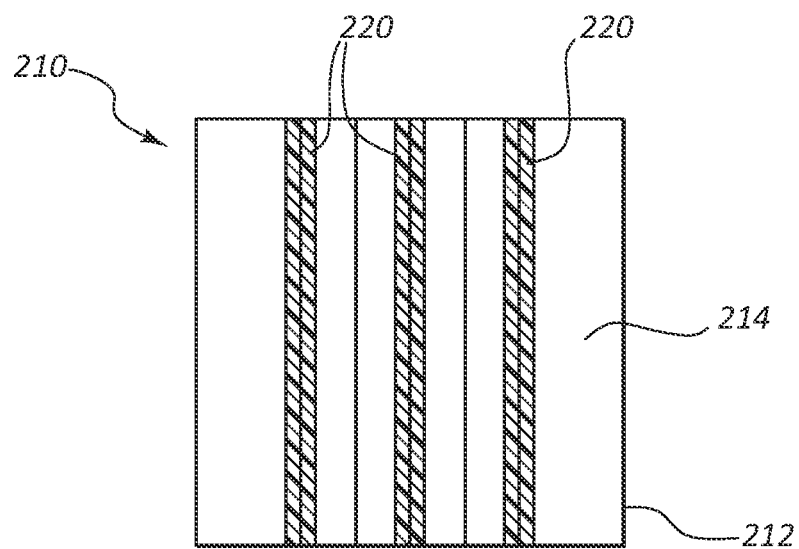

FIGS. 10A and 10B depict another example of a needle guide assembly 210, which includes a base 212 and a stepped platform 214. The platform 214 includes multiple needle guide channels 220 oriented at similar needle insertion angles but at differing distances from a needle insertion point on the skin of the patient when the needle guide assembly 210 is attached to an ultrasound probe. The differing distances of the guide channels 220 from the needle insertion site on the skin (caused by the stepped platform 214) enables each guide channel to guide a needle to a unique depth of intersection with the image plane of the ultrasound probe, and thus to targets at different subcutaneous depths. Thus, a clinician can select a desired one of the needle guide channels 220 that corresponds to the ultrasonically imaged depth of the subcutaneous target. In one embodiment, the clinician slides the ultrasound probe laterally to align the selected needle guide channel 220 with the imaged target as the needle guide assembly is not slidable in the design shown in FIGS. 10A and 10B, though the needle guide can be made movable in other embodiments. Note again that the number and indicated angles of the needle guide assembly 210 as illustrated in the accompanying figures are only examples and other configurations are, of course, possible. In another embodiment, it is appreciated that the guide channels define differing needle insertion angles independent of their separation via the stepped platform. In yet another embodiment, the guide channels are not parallel to one another, but are disposed on the platform so as to converge toward one another.

Figure 11A:
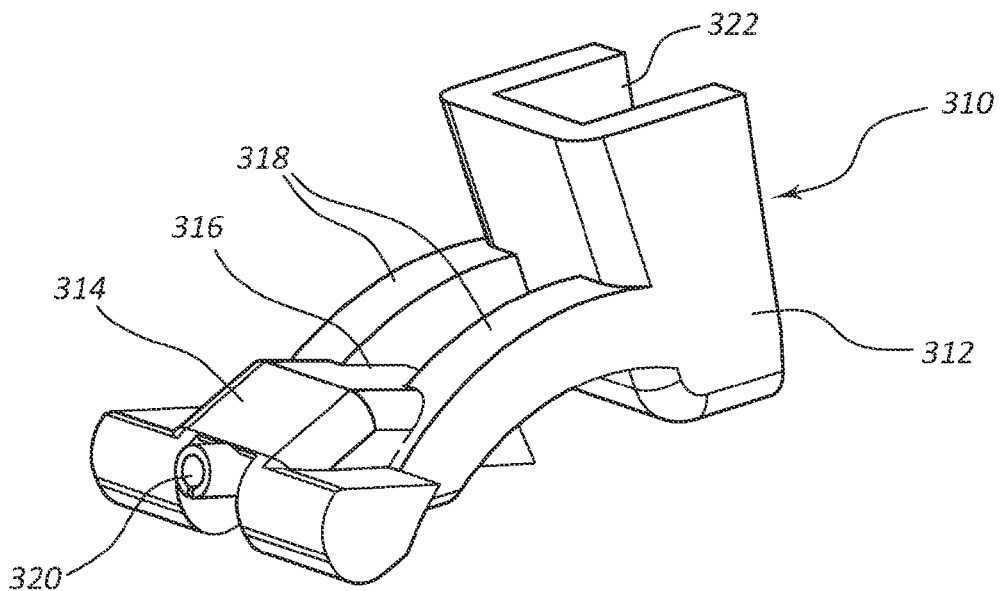
FIGS. 11A and 11B are various views of a needle guide assembly according to one embodiment.
Figure 11B:
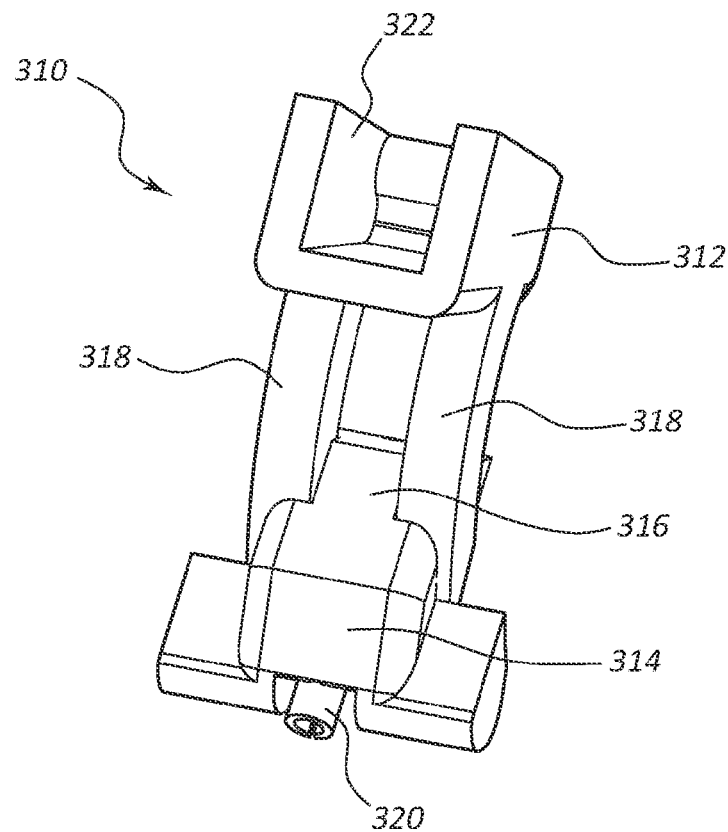

FIGS. 11A and 11B show a needle guide assembly 310 according to another embodiment, including a body 312 defining a cavity 322 for attachment to a probe, probe cap, or the like. A platform 314 including a slotted needle guide channel 320 is also included. In particular, the platform 314 includes a notched arm 316 that is slidably disposed between two arcuate rails 318 of the body 312. So configured, the platform 314 is slidable along the rails 318 to enable the insertion angle of the guide channel 320 to be modified as desired by the user so as to enable a needle inserted therein to intercept an imaged subcutaneous target, such as a vessel. In one embodiment, the insertion angle with respect to the skin of the patient can vary from about a few degrees to about 90 degrees or more. Note that depth markers can be included on the rails 318 or other portion of the needle guide assembly 310. Note further that in one embodiment the platform can be configured to be releasably lockable to the rails so as to maintain the needle guide channel at a desired angle.

Figure 12A:
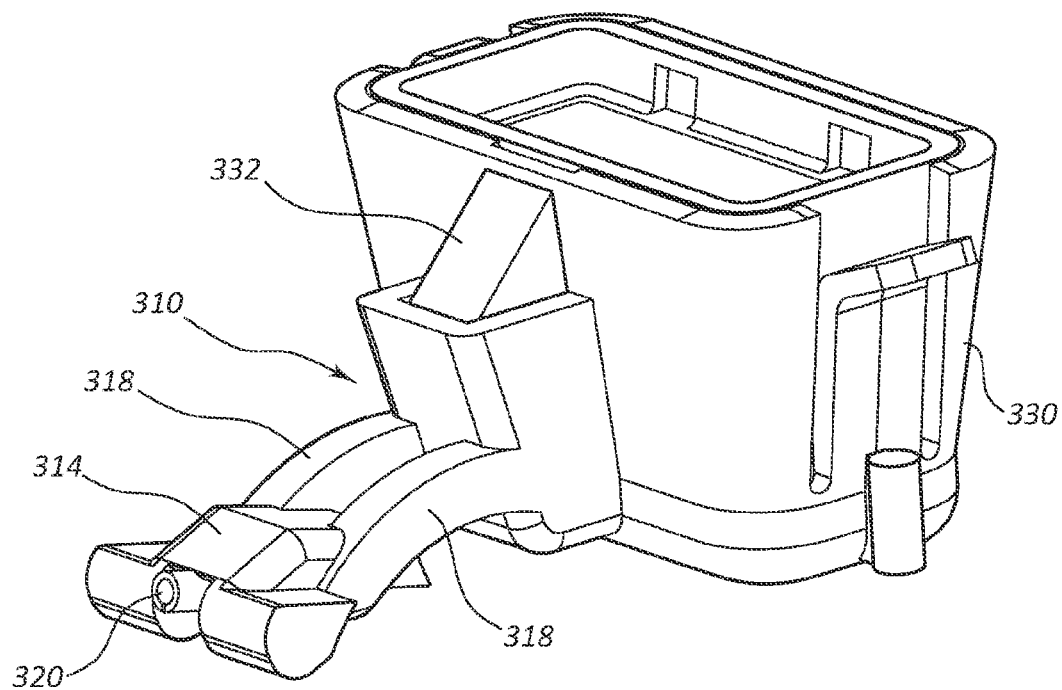
FIGS. 12A and 12B are various views of the needle guide assembly of FIGS. 11A and 11B attached to a probe cap for an ultrasound probe according to one embodiment.
Figure 12B:
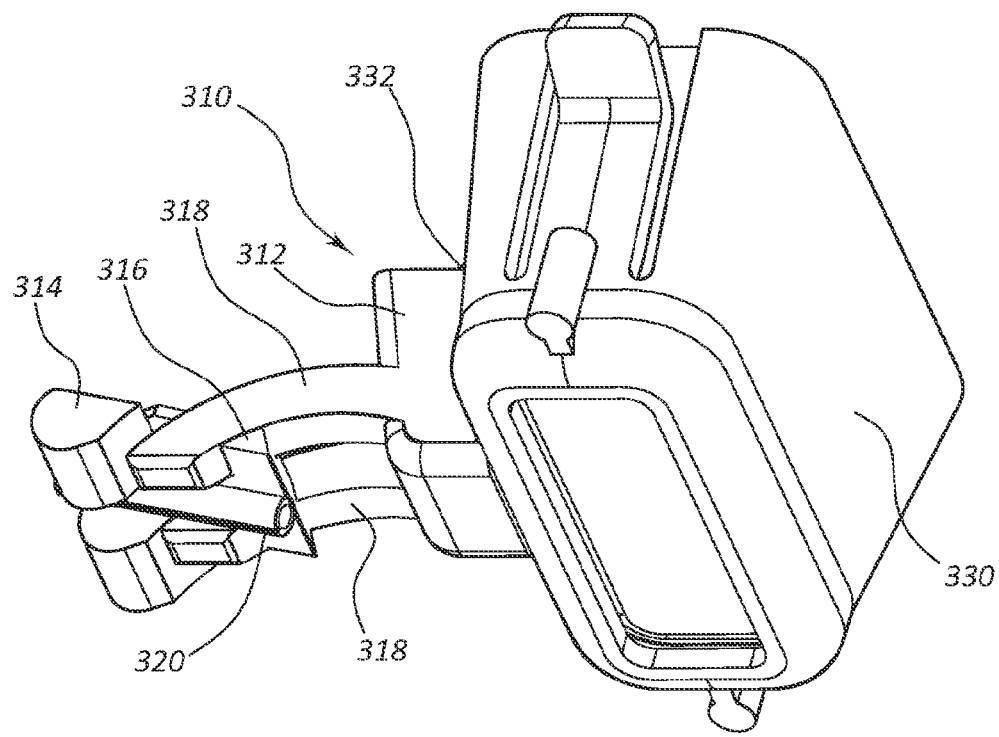

FIGS. 12A and 12B show the manner of releasable engagement of the needle guide assembly 310 with a fixture 332 of a probe cap 330, according to one possible mounting scheme. Of course, other direct or indirect engagement schemes of the probe/probe cap with this or the other needle guide assemblies disclosed herein can be employed.

Embodiments of the invention may be embodied in other specific forms without departing from the spirit of the present disclosure. The described embodiments are to be considered in all respects only as illustrative, not restrictive. The scope of the embodiments is, therefore, indicated by the appended claims rather than by the foregoing description. All changes that come within the meaning and range of equivalency of the claims are to be embraced within their scope.

What is claimed is:

1. A needle guide assembly, comprising:
an image producing device;
a needle guide body configured to at least indirectly and removably attach to the image producing device, the needle guide body laterally slidable with respect to the image producing device;
a plurality of guide channels defined by the needle guide body, each of the plurality of guide channels defining a unique insertion angle with respect to a longitudinal axis of the image producing device and configured to receive needles of differing gauges; and
a plurality of front faces that face radially outwardly away from the image producing device when attached to the image producing device, the plurality of front faces defined by the needle guide body, each of the plurality of front faces having a concavely shaped surface that slopes toward an open proximal end of one of the plurality of guide channels.

2. The needle guide assembly as defined in claim 1, wherein each of the plurality of guide channels includes two compliant arms that together define an elongate volume into which a needle is inserted, each of the compliant arms being movable upon needle insertion to increase the elongate volume when necessary to enable passage of the needle.

3. The needle guide assembly as defined in claim 2, wherein each of the compliant arms of each of the plurality of guide channels includes a notch to facilitate compliant expansion of the elongate volume of the respective guide channel, and wherein a longitudinal slot is defined between the compliant arms of each guide channel to enable a needle to be removed from the guide channel after needle insertion into a body of a patient.

4. The needle guide assembly as defined in claim 1, wherein the image producing device includes an ultrasound probe of an ultrasound imaging system, the needle guide assembly being slidably attachable to a fixture on the probe.

5. The needle guide assembly as defined in claim 1, wherein the image producing device includes an ultrasound probe of an ultrasound imaging system, the needle guide assembly being slidably attachable to a cap that is removably attached to a head portion of the probe.

6. The needle guide assembly as defined in claim 1, wherein a proximal portion of each of the plurality of guide channels extends proximally beyond a distal end of its associated one of the plurality of front faces.

7. The needle guide assembly as defined in claim 1, wherein the plurality of guide channels includes first, second, and third guide channels arranged in one of a linear and an arcuate pattern on the needle guide body.

8. A method for inserting a needle into a body of a patient using an ultrasound probe and a needle guide assembly, the needle guide assembly comprising a needle guide body movably and at least indirectly attached to the ultrasound probe, the needle guide body including a plurality of guide channels that each define a unique needle insertion angle, the method comprising:
ultrasonically imaging a subcutaneous target in the body of the patient using the probe;
laterally sliding the needle guide assembly to place in a usable position a desired one of the plurality of guide channels;
guiding a tip of the needle along a concavely shaped surface that slopes toward an open proximal end of the desired guide channel and into the open proximal end of the desired guide channel, the concavely shaped surface facing radially outwardly away from the ultrasound probe; and
inserting a needle through the desired guide channel and into the patient toward the subcutaneous target, the desired guide channel being compliant so as to accept needles of multiple gauge sizes.

9. An ultrasound imaging system, comprising:
an ultrasound probe; and
a needle guide assembly removably and at least indirectly attachable to the probe, the needle guide assembly comprising:
a needle guide body laterally slidable with respect to the probe, including a slot configured to slide along a rail on the ultrasound probe and a protrusion extending into the slot, the protrusion configured to be received in one or more openings in the rail, wherein when the protrusion is received within one of the one or more openings, the protrusion is not visible to a user of the ultrasound imaging system viewing the needle guide body; and
at least first and second elongate guide channels defined by the needle guide body, each of the guide channels defining a unique needle insertion angle, wherein a face portion proximate a proximal end of each of the guide channels is contoured so as to direct a tip of a needle into the respective guide channel.

10. The system as defined in claim 9, further comprising a cap removably attachable to a head portion of the probe, the cap including the rail along which the needle guide body is laterally slidable.

11. The system as defined in claim 10, wherein the cap and needle guide assembly are disposed before use in a sterile tray.

12. The system as defined in claim 9, wherein the needle guide body defines first, second, and third guide channels and wherein each guide channel is compliant so as to accept therein needles of differing gauges.

13. The system as defined in claim 12, wherein the face portion of each guide channel is angled according to the needle insertion angle of the respective guide channel and wherein the contour of each face is concavely shaped.

14. The system as defined in claim 9, wherein the slot is L-shaped and the rail is correspondingly L-shaped.

15. The system as defined in claim 9, wherein the protrusion is stationary within the slot.

* * * * *